US006486367B1

(12) United States Patent
Budge et al.

(10) Patent No.: US 6,486,367 B1
(45) Date of Patent: Nov. 26, 2002

(54) PROCESS FOR THE HYDROGENATION OF MALEIC ACID TO 1,4-BUTANEDIOL

(75) Inventors: John Raymond Budge, Beachwood, OH (US); Thomas George Attig, Aurora, OH (US); Robert Allen Dubbert, Solon, OH (US)

(73) Assignee: The Standard Oil Company, Chicago, IL (US)

( * ) Notice: Subject to any disclaimer, the term of this patent is extended or adjusted under 35 U.S.C. 154(b) by 574 days.

(21) Appl. No.: 08/980,542

(22) Filed: Dec. 1, 1997

(51) Int. Cl.⁷ ............................ C07C 31/18; B01J 23/40
(52) U.S. Cl. ........................................ 568/864; 502/326
(58) Field of Search ........................... 568/864; 502/326

(56) References Cited

U.S. PATENT DOCUMENTS 4,096,156 A   6/1978   Freudenberger et al. . 260/343.6
4,550,185 A   10/1985  Mabry et al. ................ 549/508
4,609,636 A   9/1986   Mabry et al. ................ 502/183
4,659,686 A   4/1987   Griffiths et al. ............. 502/183
4,973,713 A   11/1990  Manogue ..................... 549/307
4,985,572 A   1/1991   Kitson et al. ................ 549/326
5,061,671 A   10/1991  Kitson et al. ................ 502/185
5,149,680 A   9/1992   Kitson et al. ................ 502/185
5,473,086 A   12/1995  Budge et al. ................ 549/509

FOREIGN PATENT DOCUMENTS

DE    1534232      11/1978
DE    1551741      8/1979
WO    WO92/02298   2/1992

Primary Examiner—Charanjit S Aulakh
(74) Attorney, Agent, or Firm—David P. Yusko

(57) ABSTRACT

Maleic acid and/or other hydrogenatable precursors are hydrogenated in the presence of a noble metal catalyst to 1,4-butanediol. The production and yields of 1,4-butanediol are enhanced by the addition of iron to the hydrogenatable precursor feed.

12 Claims, No Drawings

PROCESS FOR THE HYDROGENATION OF MALEIC ACID TO 1,4-BUTANEDIOL

BACKGROUND OF THE INVENTION

1. Field of the Invention

This invention relates to an improved process for the hydrogenation of maleic acid, maleic anhydride or other hydrogenatable precursor to 1,4-butanediol and tetrahydrofuran. The improvement comprises the addition of iron to the maleic acid, maleic anhydride or other hydrogenatable precursor feedstock. The addition of iron in the feedstock improves catalyst performance to reaction products with higher yields of 1,4-butanediol and minimal formation of by-products.

2. Description of the Prior Art

It is well known that tetrahydrofuran, gamma-butyrolactone and 1,4-butanediol are obtained by the catalytic hydrogenation of maleic anhydride and related compounds. Tetrahydrofuran is a useful solvent for natural and synthetic resins and is a valuable intermediate in the manufacture of a number of chemicals and plastics. Gamma-butyrolactone is an intermediate for the synthesis of butyric acid compounds, polyvinylpyrrolidone and methionine. Gamma-butyrolactone is a useful solvent for acrylate and styrene polymers and also a useful ingredient of paint removers and textile assistants. 1,4-butanediol (a.k.a. 1,4-butylene glycol) is useful as a solvent, a humectant, an intermediate for plasticizers and pharmaceuticals, a cross-linking agent for polyurethane elastomers, a precursor in the manufacture of tetrahydrofuran, and is used to make terephthalate plastics.

Numerous catalysts and processes for the hydrogenation of maleic acid, maleic anhydride or other hydrogenatable precursor to tetrahydrofuran, gamma-butyrolactone and 1,4-butanediol have been disclosed. Of specific interest in the instant invention are processes which are catalyzed by a supported noble metal catalyst. It has been taught in the art that such catalysts may also contain iron.

For example, U.S. Pat. No. 4,985,572 teaches a process for the catalytic hydrogenation of a carboxylic acid or an anhydride thereof to the corresponding alcohol and/or carboxylic acid ester using a catalyst comprising rhenium, palladium and at least one other metal capable of alloying with the palladium, all on a carbon support. The preferred metal capable of alloying with the palladium is silver but gold, copper, nickel, rhodium, tin, cobalt, aluminum, manganese, gallium, iron, chromium, and platinum also are taught. The preparation of this catalyst is characterized by the simultaneous deposition of palladium and silver on the carbon support followed by a high temperature (600° C.) heat treatment. Rhenium is then deposited on the palladium/alloying metal impregnated carbon support. The resulting catalyst is then reduced.

Additionally, WO 92/02298 discloses a hydrogenation catalyst comprising palladium and rhenium and one or more metals selected from the group consisting of rhodium, cobalt, platinum, ruthenium, iron, thulium, cerium, yttrium, neodymium, aluminum, praseodymium, holmium, hafnium, manganese, vanadium, chromium, gold, terbium, lutetium, nickel, scandium and niobium, on a support.

Generally, in the hydrogenation of maleic acid, maleic anhydride or other hydrogenatable precursor, the above discussed catalysts have the propensity to produce more tetrahydrofuran and gamma-butyrolactone than 1,4-butanediol. An object of this invention is a process which will maximize 1,4-butanediol production and minimize gamma-butyrolactone production.

SUMMARY OF THE INVENTION

The instant invention is a process for the production of 1,4-butanediol comprising catalytically hydrogenating a feedstock comprising a hydrogenatable precursor and iron in contact with a hydrogen-containing gas.

DETAILED DESCRIPTION OF THE INVENTION

Maleic acid or other hydrogenatable precursor are hydrogenated in the presence of a noble metal catalyst to 1,4-butanediol. The production and yields of 1,4-butanediol are enhanced by the addition of iron or an iron containing compound to the feed.

Reactants

In the process of the instant invention, at least one hydrogenatable precursor is reacted with a hydrogen containing gas in the presence of the catalyst. As used herein a "hydrogenatable precursor" is any carboxylic acid or anhydride thereof, carboxylic acid ester, lactone or mixture thereof which when hydrogenated produces 1,4-butanediol. Representative hydrogenatable precursors include maleic acid, maleic anhydride, fumaric acid, succinic anhydride, succinic acid, succinate esters such as the $C_1$ to $C_8$ dialkyl succinates (e.g. dimethyl succinate), maleate esters such as the $C_1$ to $C_8$ dialkyl maleates (e.g. dimethyl maleate), gamma-butyrolactone or mixtures thereof The preferred hydrogenatable precursors are maleic acid, maleic anhydride, succinic acid, succinic anhydride, fumaric acid, esters of $C_4$ acids, gamma butyrolactone or mixtures thereof.

The most preferred hydrogenatable precursor is maleic acid which is typically obtained by reacting n-butane or benzene in an oxygen-containing gas in the presence of a catalyst to oxidize in the vapor phase the n-butane or benzene to maleic anhydride, and then collecting the maleic anhydride by a water quench to produce maleic acid in an aqueous solution. The oxidation of n-butane or benzene is typically operated at a temperature of about 300° C. to 600° C. and a pressure of about 0.5 to 20 atmospheres (50 to 2000 kPa).

Typically, the hydrogen ($H_2$) containing gas is commercially pure hydrogen with no diluent gases. However, the hydrogen containing gas in addition to hydrogen ($H_2$) may also contain nitrogen ($N_2$), any gaseous hydrocarbon (e.g. methane), as well as gaseous oxides of carbon, (e.g. carbon monoxide, carbon dioxide).

Catalyst

The catalyst employed in the instant invention comprises a noble metal of Group VIII of the Periodic Table selected from the group consisting of at least one of palladium, ruthenium, rhodium, osmium, iridium and platinum. These include (i) catalysts also containing at least one of rhenium, manganese or tellurium as described in UK Patent Publication No. 01551741, (ii) catalysts also containing at least one of silver and gold as described in U.S. Pat. No. 4,096,156 and (iii) catalysts also containing at least one metal capable of alloying with the noble Group VIII metal and at least one of rhenium, tungsten or molybdenum as described in U.S. Pat. No. 5,149,680. Examples of other suitable catalyst include palladium and rhenium on a carbon support as described in UK Patent Publication No. 01543232 and U.S. Pat. No. 4,659,686. These catalyst composition may also be further modified through the incorporation of a metal or metals selected from Groups IA, IIA or VIII.

The preferred catalyst employed in the instant invention comprises palladium, silver and rhenium supported on carbon. The carbons for use in this invention have a BET surface area of at least 200 m$^2$/g, and preferably be in the range of 500–1500 m$^2$/g. Catalysts of this type are described in U.S. Pat. No. 5,149,680.

The preferred catalyst composition comprises about 0.1 to about 20 weight percent palladium, preferably about 2 to about 8 weight percent palladium; about 0.1 to about 20 weight percent silver, preferably about 1 to about 8 weight percent silver; about 0.1 to about 20 weight percent rhenium, and preferably about 1 to about 10 weight percent rhenium. The ratio of palladium to silver is between 10 to 1 and 1 to 10. As suggested earlier, this catalyst composition may also be further modified through the incorporation of a metal or metals selected from Groups IA or IIA.

The preferred catalysts for use in this invention may be conveniently prepared by impregnation of the carbon support, either in single or multiple impregnation steps, with a solution or solutions containing at least one palladium, silver, or rhenium compound. As used herein, impregnation of the carbon support means to cause the carbon support to be filled, imbued, permeated, saturated or coated. The impregnating solution may optionally contain complexing agents to help solubilize one or more of the metal compounds. The catalyst is dried after each impregnation step to remove any carrier solvent. Drying temperatures are between about 80° C. and about 150° C.

In making the preferred catalysts, the solutions of palladium compound, silver compound and rhenium compound can be applied to the carbon by immersing or suspending the support material in the solution or by spraying the solution onto the carbon. The solution containing the palladium compound is typically an aqueous solution containing an amount of palladium compound to yield a catalyst product with the requisite amount of palladium. The palladium compound may be palladium nitrate or a palladium compound such as a chloride, carbonate, carboxylate, acetate, acetyl acetonate, or amine. The solution containing the silver compound is typically an aqueous one containing an amount of silver compound to yield a catalyst product with the requisite amount of silver. The palladium and silver compounds should be thermally decomposable and reducible to the metals. The solution containing the rhenium compound is typically an aqueous one containing an amount of rhenium compound to yield a catalyst product with the requisite amount of rhenium. The rhenium compound is typically perrhenic acid, ammonium perrhenate or an alkali metal perrhenate.

The impregnating solution(s) may optionally contain metal complexing agents to help solubilize one or more of the metal compounds. The addition of acetonitrile to the impregnating solution allows the Pd, Ag, and Re compounds be added in a single step. Nitric acid may also be added to the impregnating solution.

After impregnation with palladium, silver, and rhenium and drying, the preferred catalyst is activated by heating the impregnated carbon support under reducing conditions at a temperature of 120–350° C., preferably 150–300° C. Hydrogen, or a mixture of hydrogen and nitrogen, in contact with the catalyst may be conveniently used for the catalyst reduction. Reduction of the impregnated carbon support is only after the carbon support has been impregnated with palladium, silver, and rhenium. In the case of multiple impregnation steps and multiple dryings, the reduction of the catalyst is done after the final drying.

The Process

The method for carrying out the process comprises reacting a hydrogenatable precursor with a hydrogen-containing gas in the presence of iron and the hydrogenation catalyst, and recovering and purifying the reaction products by distillation.

In the instant invention, iron is added to the hydrogenatable precursor either prior to introduction of the hydrogenatable precursor to the hydrogenation reactor or in situ. Typically the iron is added as an iron salt. The iron is preferably added to the liquid hydrogenatable precursor feedstock in concentrations ranging between 1 and 10,000 ppm (weight per weight basis). Preferably the concentration of iron in the feedstock is between about 20 and 160 ppm. A wide range of iron salts may be used including iron acetate, iron propionate, iron butyrate, iron maleate, iron succinate and iron fumarate. Preferably the anion of the salt should not interfere with the hydrogenation reaction or act as a poison to the hydrogenation catalyst.

The liquid phase hydrogenation of this invention can be run using conventional apparatus and techniques in a stirred-tank reactor or in a fixed-bed reactor. Single or multiple-stage reactors may be employed. The amount of catalyst required will vary widely and is dependent upon a number of factors such as reactor size and design, contact time and the like.

The hydrogen-containing gas is fed continuously, generally with the hydrogen in considerable stoichiometric excess to the other reactants. Unreacted hydrogen can be returned to the reactor as a recycle stream. The precursor solution, e.g., maleic acid (or other hydrogenatable precursor) solution, is fed continuously at concentrations ranging from dilute solutions to near the maximum solubility level. The precursor solution may contain about 10 to about 60 weight percent maleic acid (or other hydrogenatable precursor) with the higher concentrations being more economical and preferred due to less water to recycle or dispose. Preferably the precursor solution contains about 20 to about 50 weight percent maleic acid (or other hydrogenatable precursor).

Preferably the hydrogenation step is run at a temperature of about 50° C. to 350° C., and a hydrogen pressure of about 20–400 atmospheres with hydrogen to hydrogenatable precursor ratios ($H_2$/P) of between 5 to 1 and 1000 to 1 and contact times of 0.1 minute to 20 hours.

The reaction products, 1,4-butanediol, tetrahydrofuran, gamma-butyrolactone or mixtures thereof, are advantageously separated by fractional distillation. By-products which are formed in small amounts or unreacted feed, such as for example, succinic anhydride or succinic acid, are optionally returned to the hydrogenation stage. The gamma-butyrolactone may also be recycled to the hydrogenation reactor.

Using the process of this invention, more specifically using the hydrogenation catalyst described herein, maleic acid is converted virtually quantitatively in a simple reaction. The yields of 1,4-butanediol and tetrahydrofuran achieved are about 80 mole percent or greater, typically about 90 mole percent or greater, with a majority portion of the yield being 1,4-butanediol. Reaction by-products may include n-butanol, n-butyric acid, n-propanol, propionic acid, methane, propane, n-butane, carbon monoxide, and carbon dioxide. However, the formation of non-utilizable by-products is slight.

SPECIFIC EMBODIMENTS

In order to illustrate the instant invention the following examples are provided.

EXAMPLE 1

Preparation of a Pd+Ag+Re on Carbon Catalyst 132.4 g of palladium nitrate solution (8.5 wt % Pd), 17.3 g of silver nitrate, 28 g concentrated nitric acid (70 wt %), and acetonitrile (ca. 40 cc) were placed in a 250 cc volumetric flask. The mixture was shaken to dissolve the silver nitrate, and then 45 g of perrhenic acid (53.3 wt % Re) was slowly added. Acetonitrile was then added to the flask to give exactly 250 cc of solution.

280.5 g of 1.5 mm (diameter) CECA ACL40 carbon extrudate was impregnated gradually with the above solution. The mixture was allowed to stand for 4 hours, and then dried in an oven at 120–130° C. for 20.25 hours.

For testing the catalyst extrudate was cut with a razor blade so that the maximum length of the extrudate was about 1.5 mm.

EXAMPLE 2

Hydrogenation of Aqueous Maleic Acid and Catalyst Testing

The catalyst of Example 1 was tested in two Hasteloy C276 reactors connected in series using heated Hasteloy C276 tubing. The reactors had an internal diameter of 0.516", and each was fitted with a ⅛" axial Hasteloy C276 thermowell.

The catalyst was mixed with 50/70 mesh quartz chips (0.625 g quartz per g of catalyst) before charging to the reactor. 20 cc (12.15 g) of catalyst was placed in the first reactor, and 40 cc (24.3 g) in the second reactor. Prior to testing the catalyst was reduced at atmospheric pressure in flowing hydrogen (400 sccm) by heating the catalyst gradually to 230° C. over approximately 13 to 18 hours and then maintaining the catalyst at 230° C. for approximately 5 hours.

Extensive testing of the catalyst was carried out over several thousand hours at pressures of 2500 to 4000 psig. The reactors were operated with hydrogen recycle. A small portion of the hydrogen was vented to prevent the accumulation of non-condensable gases. The aqueous Maleic acid feed which was used for the iron addition study contained small amounts of other organic acids as summarized in Table 1. Iron was added to the maleic acid in the form of iron (II) acetate to yield a 40 ppm (w/w) iron containing solution. The iron readily dissolved in the solution. The effect of the iron addition to the maleic acid feed was evaluated between 4450 and 4550 hours on stream, with the following process conditions:

Pressure: 4000 psig
$H_2$/(MAC+FAC) Feed Ratio: 92
$H_2$ Make-up to Recycle Ratio: 0.083
First Reactor:
   Average Set Temperature: 130° C.
Second Reactor:
   Average Set Temperature: 162° C.

Table 2 summarizes the results of the testing with and without iron added to the maleic acid feed. Product selectivity's were calculated on a molar $C_4$ basis. The BDO yield was significantly higher for iron added to the maleic acid feed.

TABLE 1

Composition of Maleic Acid Feed

| Component | wt % |
|---|---|
| Maleic Acid | 33.4 |
| Fumaric Acid | 0.41 |
| Acrylic Acid | 0.21 |
| Acetic Acid | 0.72 |
| Malic Acid | 0.40 |

TABLE 2

Catalyst Performance (Selectivity) Data

| | % BDO | % THF | % GBL | % BuOH | % PrOH | % SAC |
|---|---|---|---|---|---|---|
| Iron Added | 69.2 | 19.75 | 5.38 | 2.86 | 0.63 | 2.04 |
| No Iron Added | 61.7 | 28.02 | 4.63 | 3.11 | 0.63 | 1.74 | wherein:
BDO = 1,4-butanediol
THF = tetrahydrofuran
GBL = gamma-butyrolactone
BuOH = butanol
PrOH = propanol
SAC = succinic acid It is to be understood that the subject invention is not to be limited by the examples set forth herein. These have been provided merely to demonstrate operability, and the selection of catalysts, metal sources, carbon supports, concentrations, contact times, solids loadings, feedstocks, reaction conditions, and products, if any, can be determined from the total specification disclosure provided, without departing from the spirit of the invention herein disclosed and described, the scope of the invention including modifications and variations that fall within the scope of the attached claims.

The claimed invention is:

1. A process for the production of 1,4-butanediol comprising catalytically hydrogenating a hydrogenatable precursor in contact with a hydrogen-containing gas and a hydrogenation catalyst comprising at least one noble metal of Group VIII of the Periodic Table, selected from the group consisting of palladium, ruthenium, rhodium, osmium, iridium and platinum wherein iron is added to the hydrogenatable precursor.

2. The process of claim 1 wherein the hydrogenatable precursor is selected from the group consisting of maleic acid, maleic anhydride, fumaric acid, succinic acid, succinic anhydride, $C_1$ to $C_8$ dialkyl succinates, $C_1$ to $C_8$ dialkyl maleates, gamma-butyrolactone and mixtures thereof.

3. The process of claim 2 wherein the hydrogenatable precursor is at least one of maleic acid, succinic acid, or gamma-butyrolactone.

4. The process of claim 1, wherein the noble metal of Group VIII is selected from the group consisting of palladium, platinum, rhodium and ruthenium.

5. The process of claim 1, wherein the hydrogenation catalyst comprises palladium and rhenium.

6. The process of claim 1, wherein the hydrogenation catalyst comprises palladium, rhenium and silver on a carbon support.

7. The process of claim 1, wherein the iron is an iron salt selected from the group of iron acetate, iron propionate, iron butyrate, iron maleate, iron succinate, iron fumarate, and mixtures thereof.

8. The process of claim 1, wherein the iron is added to the hydrogenatable precursor in concentrations ranging between 1 and 10,000 ppm (weight per weight basis).

9. The process of claim 1, wherein the iron is added to the liquid hydrogenatable precursor in concentrations ranging between about 20 and about 160 ppm (weight per weight basis).

10. The process of claim 1, wherein the ratio of hydrogen to hydrogenatable precursor is between about 5 to 1 and about 1000 to 1.

11. The process of claim 1, wherein the hydrogen-containing gas pressure is between about 20 and 400 atmospheres.

12. The process of claim 1, wherein the contact time is between about 0.1 minute and 20 hours.

* * * * *

UNITED STATES PATENT AND TRADEMARK OFFICE
CERTIFICATE OF CORRECTION

PATENT NO.     : 6,486,367 B1                                                              Page 1 of 1
DATED          : November 26, 2002
INVENTOR(S)    : John Raymond Budge, Thomas George Attig and Robert Allen Dubbert It is certified that error appears in the above-identified patent and that said Letters Patent is hereby corrected as shown below:

Column 2,
Line 32, "mixtures thereof The preferred" should read -- mixtures thereof. The preferred --

Column 3,
Line 2, "These catalyst composition may" should read -- These catalyst compositions may --
Line 8, "and preferably be in the" should read -- and preferably are in the --
Lines 58-59, "compounds be added in" should read -- compounds to be added in --

Column 5,
Lines 15-16, "Re) was slowly added." should read -- Re) were slowly added. --
Line 38, "of catalyst was placed in" should read -- of catalyst were placed in --
Line 49, "aqueous Maleic acid" should read -- aqueous maleic acid --
Line 66, "Product selectivity's were" should read -- Product selectivities were --

Column 6,
Line 1, "Product selectivity's were" should read -- Product selectivities were --
Line 25, "BDO = 1,4-butandiol" should read -- BDO = 1,4-butanediol --

Signed and Sealed this

Fifth Day of August, 2003

JAMES E. ROGAN
*Director of the United States Patent and Trademark Office*